(12) United States Patent
Commarieu

(10) Patent No.: US 7,227,046 B2
(45) Date of Patent: Jun. 5, 2007

(54) METHOD FOR MAKING BISPHENOL A

(75) Inventor: Annie Commarieu, Pau (FR)

(73) Assignee: Arkema, Paris, La Defense, Cedex (FR)

( * ) Notice: Subject to any disclaimer, the term of this patent is extended or adjusted under 35 U.S.C. 154(b) by 628 days.

(21) Appl. No.: 10/466,814

(22) PCT Filed: Jan. 8, 2002

(86) PCT No.: PCT/FR02/00042

§ 371 (c)(1),
(2), (4) Date: Dec. 19, 2003

(87) PCT Pub. No.: WO02/059069

PCT Pub. Date: Aug. 1, 2002

(65) Prior Publication Data

US 2004/0110992 A1   Jun. 10, 2004

(30) Foreign Application Priority Data

Jan. 23, 2001 (FR) .................................. 01 00882

(51) Int. Cl.
*C07C 39/12* (2006.01)
*C07C 39/16* (2006.01)
(52) U.S. Cl. ....................... 568/727; 568/728
(58) Field of Classification Search ............... 568/727, 568/728
See application file for complete search history.

(56) References Cited

U.S. PATENT DOCUMENTS 4,517,387 A * 5/1985 Matsunaga et al. ......... 568/728

5,777,180 A * 7/1998 June et al. .................. 568/728
6,465,697 B1 * 10/2002 Palmer et al. .............. 568/728

FOREIGN PATENT DOCUMENTS

AU  474 155   7/1975
AU  474155  * 6/1976

OTHER PUBLICATIONS

"Mercaptals", IUPAC Compendium of Chemical Terminology, Electronic Version, 1997, URL:http://goldbook.iupac.org/M03830.pdf.
"Mercaptoles", IUPAC Compendium of Chemical Terminology, Electronic Version, 1997, URL:http://goldbook.iupac.org/M03830.pdf.

* cited by examiner

*Primary Examiner*—Thurman K. Page
*Assistant Examiner*—Lalitha Nagubandi
(74) *Attorney, Agent, or Firm*—Millen, White, Zelano, Branigan, P.C.

(57) ABSTRACT

The continuous process for manufacturing bisphenol A according to the invention, by reacting phenol and acetone in the presence of a strong acid catalyst and a co-catalyst, is carried out using as co-catalyst a dithio ether of general formula:

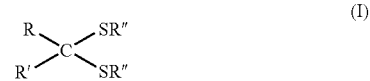

in which the symbols R and R' each represent a hydrogen atom, an alkyl radical or a phenyl radical, and the symbol R" represents an optionally substituted alkyl radical.

30 Claims, 1 Drawing Sheet

METHOD FOR MAKING BISPHENOL A

The present invention relates to the field of bisphenols and its subject is, more particularly, the manufacture of bisphenol A (4,4'-isopropylidene-diphenol).

Bisphenol A is the bisphenol which is most commonly used industrially. Produced in more than one million tons, it is mainly used as an intermediate in the manufacture of plastics, especially that of polycarbonates, epoxy resins and polyesters.

Bisphenol A is a product which has been known for a long time and there is an abundance of literature relating to its synthesis (see, for example, Ullmann's Encyclopaedia of Industrial Chemistry 5th edition, Vol. A 19, pp. 350–351). Industrially, bisphenol A is usually obtained by condensing one mole of acetone with two moles of phenol according to the reaction:

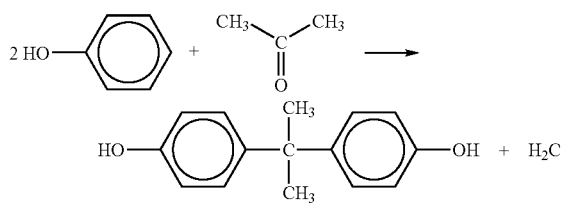

This reaction is generally carried out in the presence of a strong acid catalyst (HCl or a sulphonic resin) and a mercaptan co-catalyst such as methyl mercaptan (MM) or 3-mercaptopropionic acid. In the absence of a mercaptan catalyst, the reaction is possible, but it is slower and less selective, the 2,4' isomer then forming more readily.

Figure 1:
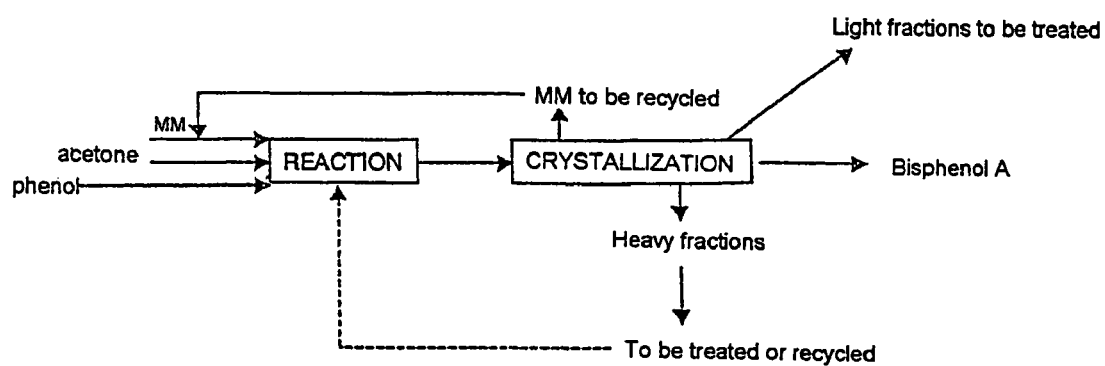

The attached FIG. 1 is a flow diagram of a conventional industrial process for manufacturing bisphenol A. This process essentially comprises a reaction zone fed with acetone, phenol, strong acid and mercaptan (fresh and recycled) and a zone for crystallizing the bisphenol A with means for separating the light and heavy fractions and for recycling the mercaptan (MM).

In such a process, the mercaptan cannot all be recycled and it is necessary to introduce a supply of fresh mercaptan, this supply possibly being up to 99% of the total amount required.

Unfortunately, due to its high toxicity, deliveries of methyl mercaptan pose safety problems which are such that bisphenol A manufacturers who use methyl mercaptan as co-catalyst are searching for solutions to replace methyl mercaptan. Thus, it has been proposed in patent U.S. Pat. No. 4,517,387 to replace the methyl mercaptan feed with a direct injection of sodium methyl mercaptide (SMM) in the reaction to synthesize bisphenol A. This procedure appears to be difficult to use at the industrial scale since it can generate a deposit of sodium salts in the reactor. Another solution which has been envisaged would consist in generating, in a specific plant at the user's site, methyl mercaptan from SMM before injecting it into the bisphenol A synthesis reactor. However, this solution is relatively cumbersome to implement since it requires the installation of an additional reactor to neutralize the SMM with a strong acid and generates malodorous saline aqueous effluents.

It has now been found that the problem may be solved by replacing methyl mercaptan with a dithio ether of general formula (I), this product being obtained by condensing one molecule of a carbonyl derivative (II) with two molecules of a mercaptan (III):

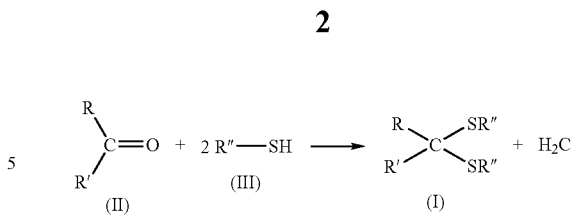

When synthesized ex situ at the mercaptan production site, the dithio ethers are products that are easy to handle. Being liquid at the temperatures usually used for the synthesis of bisphenol A (25–180° C.), the liquid dithio ethers may be introduced directly into the bisphenol A synthesis reactor using a metering pump; their use does not therefore necessitate any substantial modification of the existing bisphenol A manufacturing plant. Furthermore, in contrast with SMM, dithio ethers have the advantage of not generating malodorous alkaline effluents.

One subject of the invention is thus a continuous process for manufacturing bisphenol A by reacting phenol and acetone in the presence of a strong acid catalyst and a co-catalyst, characterized in that a dithio ether of general formula (I) is used as co-catalyst. In this formula, and also in formulae (II) and (III), the symbols R and R', which may be identical or different, each represent a hydrogen atom, a linear or branched alkyl radical containing from 1 to 12 carbon atoms (preferably 1 to 4) or a phenyl radical, and the symbol R" represents a linear or branched alkyl radical containing from 1 to 12 carbon atoms (preferably 1 to 4) and optionally substituted with a carboxylic acid group.

So as not to stray too far from processes using methyl mercaptan as co-catalyst, dithio ethers derived from methyl mercaptan (R"=$CH_3$) are preferred. The dithio ethers obtained by condensing formaldehyde (R=R'=H) or acetone (R=R'=$CH_3$) with methyl mercaptan or 3-mercaptopropionic acid are particularly suitable. The dithio ethers that are more especially preferred are 2,2-bis(methylthio) propane (also known as 3,3-dimethyl-2,4-dithiapentane and referred to hereinbelow by the abbreviation BMTP) which is the product of condensation of one molecule of acetone with two molecules of methyl mercaptan:

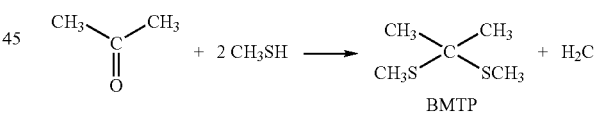

and bis(methylthio)methane (also known as 2,4-dithiapentane and referred to hereinbelow by the abbreviation BMTM) which is the product of condensation of one molecule of formaldehyde with two molecules of methyl mercaptan:

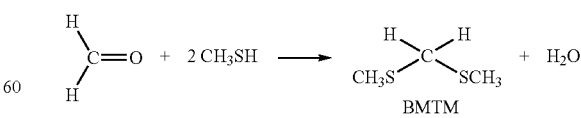

These two dithio ethers have the following characteristics:

|  | BMTM | BMTP |
| --- | --- | --- |
| Crystallization temperature | <0° C. | −18° C. |
| Boiling point | 147° C. | 155° C. |

BMTP and BMTM may be considered as equivalents of methyl mercaptan. They may thus be used in an existing plant for manufacturing bisphenol A under the same conditions as methyl mercaptan, working at an isoconcentration of sulphur in the reaction mixture. Given that one mole of thio ether corresponds to two moles of methyl mercaptan, 1 kg of BMTP is equivalent, in activity, to 0.7 kg of methyl mercaptan and 1 kg of BMTM is equivalent, in activity, to 0.88 kg of methyl mercaptan.

Given that, in a conventional industrial process for manufacturing bisphenol A, the methyl mercaptan concentration of the reaction mixture is between 1 mol % and 100 mol % relative to the strong acid catalyst (sulphonic resin, hydrochloric acid or sulphuric acid), the amount of dithio ether to be used will be between 0.5 mol % and 50 mol % relative to the strong acid catalyst, and preferably between 2.5 mol % and 25 mol %.

The dithio ethers used may be synthesized by any known means, but they are advantageously synthesized by injecting the mercaptan (III) into the carbonyl derivative (II) at room temperature in the presence of a strong acid catalyst such as hydrochloric acid, sulphuric acid or an acidic solid such as a sulphonic resin (for example the resin Amberlyst® 15) or a zeolite, followed by removing any excess carbonyl derivative and the water produced on a rotary evaporator or by distillation. The reaction mixture at the end of the synthesis is composed essentially of the dithio ether, water and unreacted carbonyl derivative. It may also be injected as is (i.e. the dithio ether mixed with the water and the carbonyl derivative) into the bisphenol A process (especially when the dithio ether is BMTP since all the components of the mixture are present in the reaction medium).

In the process according to the invention, bisphenol A is synthesized under exactly the same operating conditions as those used when the co-catalyst is methyl mercaptan, namely:

phenol/acetone molar ratio: 1 to 50 and preferably 5 to 20
temperature: 25–180° C. and preferably 40 to 160° C.
pressure: 0.5–20 bar and preferably 1 to 10 bar
contact time: 5–180 minutes and preferably 10 to 120 minutes.

Given that during the reaction the BMTP generates methyl mercaptan, the usual separation train can be used without any modification to collect the gaseous effluents and then to recycle or neutralize with sodium hydroxide.

Figure 2:
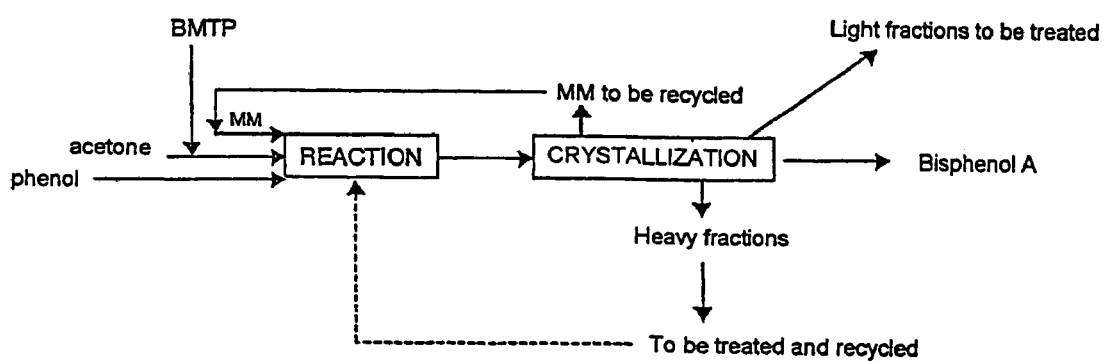

As mentioned above, the replacement of methyl mercaptan with BMTP does not require any substantial modifications to the existing plant for manufacturing bisphenol A, the only modification being, as shown in the attached FIG. 2, a liquid BMTP inlet instead of a methyl mercaptan inlet.

In accordance with one particular embodiment of the process according to the invention, the injection of pure BMTP may be replaced with that of a mixture, of BMTP, acetone and water, such as, for example, that resulting from the ex situ synthesis of BMTP by reacting methyl mercaptan with an excess of acetone. It suffices to take account of the acetone present in this mixture in order to adjust the feed of fresh acetone to the reactor. The BMTP-acetone-water mixture is just as easy to transport as pure BMTP, and the operation to purify the BMTP is thus avoided.

Similarly, the injection of pure BMTM may be replaced with that of a mixture of BMTM, formaldehyde and water, such as that resulting from the ex situ synthesis of BMTM by reacting methyl mercaptan with an excess of formaldehyde.

The invention claimed is:

1. Continuous process for manufacturing bisphenol A by reacting phenol and acetone in the presence of a strong acid catalyst and a co-catalyst, characterized in that a dithio ether of general formula:

in which the symbols R and R', which may be identical or different, each represent a hydrogen atom, a linear or branched alkyl radical containing from 1 to 12 carbon atoms or a phenyl radical, and the symbol R" represents a linear or branched alkyl radical containing from 1 to 12 carbon atoms and optionally substituted with a carboxylic acid group; is used as co-catalyst.

2. Process according to claim 1, in which the alkyl radicals of the dithio ether contain from 1 to 4 carbon atoms.

3. Process according to claim 1, in which the dithio ether is a methyl mercaptan derivative.

4. Process according to claim 3, in which the dithio ether is 2,2-bis (methylthio) propane.

5. Process according to claim 4, in which pure 2,2-bis (methylthio) propane is used.

6. Process according to claim 4, in which a mixture of 2,2-bis (methylthio) propane, acetone and water is used.

7. Process according to claim 6, in which the mixture is that resulting from the ex situ synthesis of 2,2-bis(methylthio)propane by reacting methyl mercaptan with acetone.

8. Process according to claim 3, in which the dithio ether is bis (methylthio) methane.

9. Process according to claim at 8, in which pure bis (methylthio) methane is used.

10. Process according to claim 8, in which a mixture of bis (methylthio) methane, formaldehyde and water is used.

11. Process according to claim 10, in which the mixture is that resulting from the ex situ synthesis of bis(methylthio) methane by reacting methyl mercaptan with formaldehyde.

12. Process according to claim 1, in which the amount of dithio ether used is between 0.5 mol % and 50 mol % relative to the strong acid catalyst.

13. Process according to claim 1, which is performed at a temperature of between 25 and 180° C.

14. Process according to claim 1, in which the working pressure is between 0.5 and 20 bar.

15. Process according to claim 1, in which the contact time is between 5 and 180 minutes.

16. A process according to claim 12, in which the amount of dithio ether used is between 2.5 mol % and 25 mol % relative to the strong acid catalyst.

17. Process according to claim 13, which is performed at a temperature of between 40 and 160° C.

18. Process according to claim 14, in which the working pressure is between 1 and 10 bar.

19. Process according to claim 15, in which the contact time is between 10 and 120 minutes.

20. A continuous process for manufacturing bisphenol A comprising reacting phenol and acetone in the presence of an acid catalyst and a co-catalyst, wherein said co-catalyst is a dithio ether of the formula:

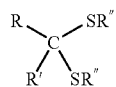

(I)

in which
R and R', which may be identical or different, are each a hydrogen atom, linear or branched alkyl containing from 1 to 12 carbon atoms, or phenyl, and
R" is a linear or branched alkyl containing from 1 to 12 carbon atoms which is optionally substituted with a carboxylic acid group.

21. A process according to claim 20, wherein said dithio ether is 2,2-bis (methylthio) propane.

22. A process according to claim 20, wherein R and R', which may be identical or different, are each a linear or branched alkyl containing from 1 to 12 carbon atoms, or phenyl, and R" is a linear or branched alkyl containing from 1 to 12 carbon atoms.

23. A process according to claim 21, wherein said dithio ether is 2,2-bis (methylthio) propane.

24. A process according to claim 20, wherein R and R', which may be identical or different, are each a linear or branched alkyl containing from 1 to 4 carbon atoms, or phenyl, and R" is a linear or branched alkyl containing from 1 to 4 carbon atoms.

25. A process according to claim 24, wherein said dithio ether is 2,2-bis (methylthio) propane.

26. A process according to claim 20, wherein said acid catalyst is a sulphonic resin, hydrochloric acid, or sulphuric acid.

27. A process according to claim 26, wherein said dithio ether is 2,2-bis (methylthio) propane.

28. A process according to claim 21, wherein said co-catalyst is pure 2,2-bis (methylthio) propane is used.

29. A process according to claim 21, wherein said co-catalyst is a mixture of 2,2-bis (methylthio) propane, acetone and water.

30. A process according to claim 29, wherein said mixture is that resulting from ex situ synthesis of 2,2-bis(methylthio) propane by reacting methyl mercaptan with acetone.

* * * * *